(12) United States Patent
Carden

(10) Patent No.: US 6,284,014 B1
(45) Date of Patent: *Sep. 4, 2001

(54) METAL MATRIX COMPOSITE

(75) Inventor: Robin Carden, Irvine, CA (US)

(73) Assignee: Alyn Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/436,801

(22) Filed: Nov. 8, 1999

Related U.S. Application Data

(63) Continuation-in-part of application No. 08/836,010, filed on May 6, 1997, now Pat. No. 5,980,602, which is a continuation-in-part of application No. 08/536,695, filed on Sep. 29, 1995, now Pat. No. 5,669,059, which is a division of application No. 08/183,728, filed on Jan. 19, 1994, now Pat. No. 5,486,223.

(51) Int. Cl.$^7$ ....................................... B22F 1/00

(52) U.S. Cl. ................................. 75/252; 75/254

(58) Field of Search .................. 75/236, 252, 254

(56) References Cited

U.S. PATENT DOCUMENTS

| | | | |
|---|---|---|---|
| 5,486,223 | * | 1/1996 | Carden ................... 75/244 |
| 5,669,059 | * | 9/1997 | Carden ................... 419/12 |
| 5,980,602 | * | 11/1999 | Carden ................... 75/236 |

* cited by examiner

Primary Examiner—Daniel Jenkins
(74) Attorney, Agent, or Firm—Cooper & Dunham LLP

(57) ABSTRACT

An extrudable and weldable matrix alloy composite comprising: a) a base material metal of about 50 to 99.9% by weight, b) boron carbide or silicon carbide of about 0.1 to 50% by weight, c) less than about 3.0% by weight of at least one metal having an intermetallic phase temperature lower than the melting point of the base material metal, and d) a reinforcement agent of up to about 5% by weight.

30 Claims, 13 Drawing Sheets

FIGURE 5   7093Al - ELASTIC MODULUS VS. VOL%SiC

METAL MATRIX COMPOSITE

CROSS-REFERENCE

This is a continuation-in-part of application Ser. No. 08/836,010 filed on May 6, 1997 now U.S. Pat. No. 5,980,602 which is a continuation-in-part of application Ser. No. 08/536,695 filed on Sep. 29, 1995 now U.S. Pat. No. 5,669,059 which, in turn, is a divisional application of Ser. No. 08/183,728, filed on Jan. 19, 1994 now U.S. Pat. 5,486,223.

BACKGROUND OF THE INVENTION

1. Field of the Invention

The present invention relates generally to metal matrix compositions. Such compositions or composites comprise one or more base material metals such as, for example, aluminum, titanium, or magnesium, to which is added a selected percentage of ceramic material to alter the properties of the base material metal(s) in a positive manner. Strength, hardness, and drawability are increased. Drawability facilitates fabrication of various articles of manufacture from such composite materials. More specifically, the present invention pertains to an improved metal matrix composite which, in a preferred embodiment, uses boron carbide as the added ceramic material. The composites result from a novel method of manufacture producing a composite which is lighter, stronger, stiffer, and which has a higher fatigue strength than other available alloys of the base material metal, and which is also lighter, stronger, stiffer, and which has a higher fatigue strength than prior art metal matrices, composites, and particularly those metal matrix composites which are of comparable cost.

2. Prior Art

In recent years metal matrix compositions or composites have become popular materials for a variety of applications. This new family of materials has become popular because of improvements in stiffness, strength, and wear properties. Basic metal matrix composites are made typically with aluminum, titanium, or magnesium as the base material metal. Then certain percentages of ceramics are added. Typical ceramics include boron carbide, silicon carbide, titanium diboride, titanium carbide, aluminum oxide, and silicon nitride. Most known metal matrix composites are made by introducing the ceramics into the molten metal. In large production runs of metal matrix composites, the ceramic reinforcement must be wetted by the liquid metal to facilitate incorporation of the reinforcement into the melt. In those metal matrix composites using silicon carbide and aluminum, the silicon carbide is thermodynamically unstable in molten aluminum which leads to the formation of aluminum carbide at the interface and increased concentration of silicon in the material matrix during the solidification process. This interface reaction is believed to have detrimental effects on the mechanical properties of the resulting composite by reducing the interface strength and changing the composition.

Recently, powder metallurgy consolidation has emerged as a competing method of fabricating metal matrix composites by consolidating the powders by means of hot pressing and conventional powder metallurgy operations with vacuum sintering used to achieve a high density green body. By following certain isopressing and sintering techniques, a 99% theoretical density billet can be achieved.

In the present invention, it has been found that the most desirable ceramic candidate for metal matrix composites is boron carbide or silicon carbide. Boron carbide is the third hardest material known and the hardest material produced in tonnage. Boron carbide powders can be formed by a variety of reactions including the carbon reduction of any of several boron-oxygen compounds including boric oxide, borax, boracite, as well as by the direct combination of the elements. Usually, most commercial boron carbide is produced in arc furnaces. Boric acid is added together with carbon in the form of coke and heated to very high temperatures. An electric arc is maintained between graphite electrodes inside a furnace. The synthesis reaction is accompanied by the release of large volumes of carbon monoxide. Venting and disposal of the carbon monoxide gas constitutes a major design consideration. Boron carbide is also the lightest of the ceramics typically used in metal matrix composite technology, but it is very hard and expensive. Its hardness limits its extrudability. Thus it would be highly advantageous if it were possible to produce an improved metal matrix composite which utilizes an advanced ceramic such as boron carbide but which, unlike the prior art, results in an extrudable composite material that allows easy fabrication of various articles of manufacture so that such resulting articles have the specific strength and stiffness improvements as compared to equivalent articles of manufacture using only the base material metals.

SUMMARY OF THE INVENTION

The present invention comprises an improved metal matrix composite which, in a preferred embodiment disclosed herein, utilizes boron carbide as the ceramic additive to a base material metal. The fabrication process is unlike that of a number of other metal matrix composites because it is not made through molten processes. More specifically, instead of melting the boron carbide or silicon carbide with the aluminum, nickel, zinc, magnesium, titanium, or other base material metal, the metal matrix composite of the present invention begins with the blending of powders of all the various elements such as by means of a jet mill which is basically an air blaster used to uniformly mix powdered substances and avoid stratification and settling. After the particles have been sufficiently mixed, they are directed into a die and then into a cylindrical container where the particulates are subjected to extremely high pressures transforming the elements into a solid ingot. It is from these ingots that the extrusion tubes or other articles of manufacture may then be made. The resulting advanced metal matrix composites of the boron carbide embodiment of the invention are 60% lighter, 30% stronger, 40–45% stiffer, and 50% higher in fatigue strength than any of the top of the line 7000 series aluminum alloy materials. In addition, the inventive material is 7–8% lighter, 26% stronger, 5% stiffer, and has 35–40% greater fatigue strength than most popular metal matrix composites available in the prior art. In one embodiment disclosed herein, the base material metal is preferably aluminum, magnesium, or titanium, or an alloy thereof, provided in powder form and preferably being approximately 97% pure with the balance of the material comprising various trace metals such as chromium, copper, iron, magnesium, silicon, titanium, and zinc. The boron carbide powder is 99.5% pure boron carbide having a particulate size in the range of 2–19 microns with a mean or average size of approximately 8.4 microns.

In one typical embodiment of the invention, the metal base material was selected from an aluminum alloy 6061T-6 to which was added approximately 12% by weight the aforementioned boron carbide powder which included silicon in an amount of 0.1–0.4%, iron in the amount of 0.05–0.4%, and aluminum in the amount of 0.05–0.4%. The underlying boron carbide material was approximately 77% boron content and 22% carbon content.

A metal matrix composite made from the aforementioned materials in accordance with the fabrication process of the present invention to be described hereinafter, typically may result in a composite material which exhibits a tensile strength of about 62–108 kpsi, a yield strength of about 58–97 kpsi, and a modulus of elasticity of about 10.0–14.50 Mpsi, Although higher or lower strengths are possible. Furthermore, the resulting material is approximately as hard as chromoly steel but has a density which is even lower than aluminum alloy.

Importantly, the material of the present invention is readily extrudable. Ingots of the metal matrix composites of the present invention are extruded through a titanium diboride die bearing material which exhibits a significant increase in die insert life. The die bearing material alternatively may be tungsten carbide, tungsten carbide composite, boron carbide, carbon nitride, a plasma vapor deposited ceramic such as titanium carbide or a chemically deposited ceramic such as titanium nitride. Furthermore, the present invention is readily weldable. In fact, the coated boron carbide particulates of the material disclosed herein tend to flux and move into the weld pool which creates a very strong weld joint. Thus the present invention is not only highly suited for the manufacture of various shaped articles, but is also suited for interconnecting such articles by conventional welding processes as will be hereinafter more fully explained.

OBJECTS OF THE INVENTION

Figure 1:
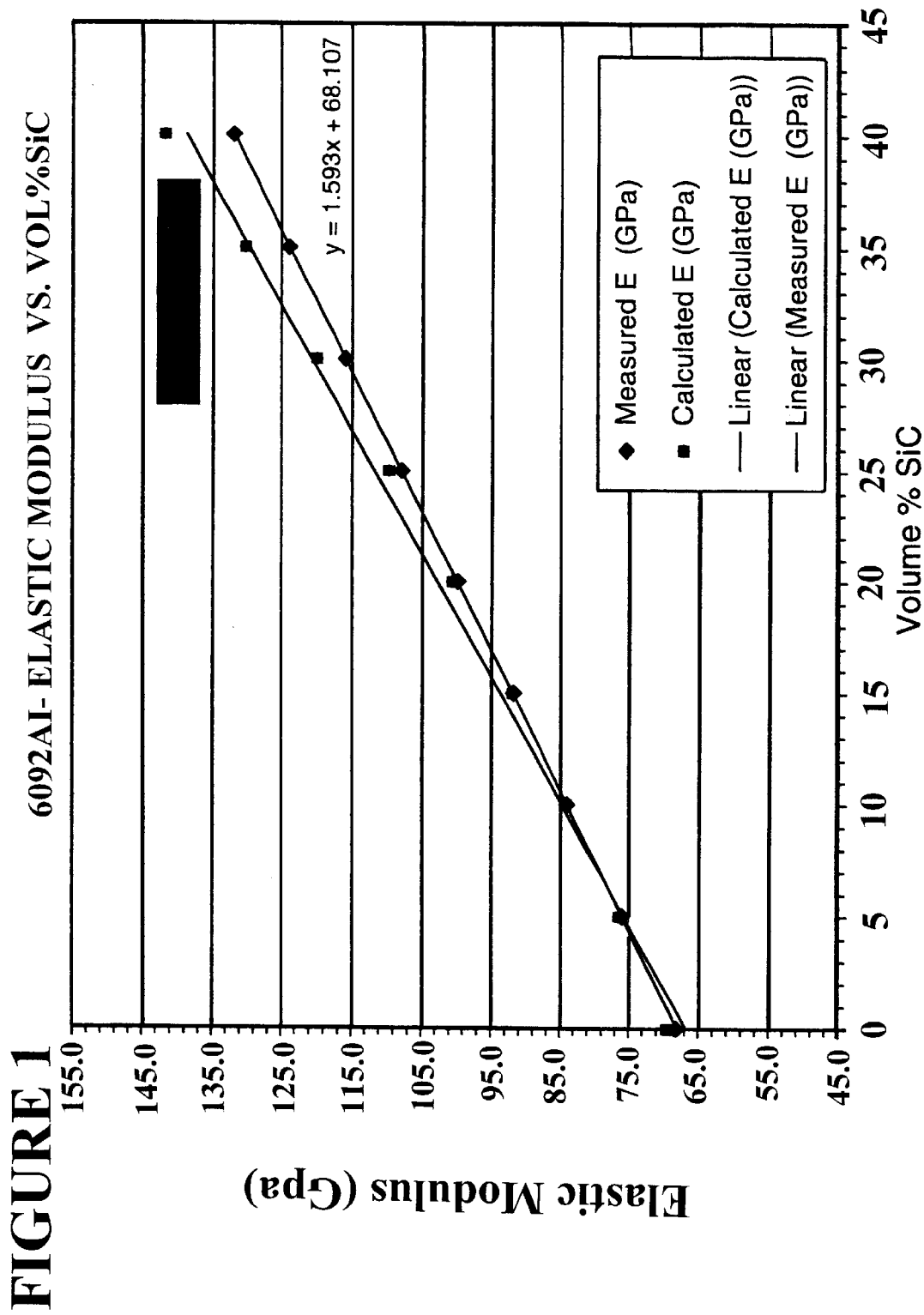
FIG. 1 is a graph of elastic modulus (GPa) of matrix alloy composites of 6092 aluminum alloy as a function of SiC content.

It is a principal object of the present invention to provide an improved metal matrix composite material which exhibits certain advantageous properties and manufacturability conducive to the fabrication of certain articles of manufacture having improved characteristics such as reduced weight, higher strength, and increased hardness.

It is an additional object of the present invention to provide an improved metal matrix composite material which is especially adapted for use as structural members in lightweight applications such as bicycle frames and the like while retaining or improving the strength and hardness at the same relative cost of comparable materials used in similar structures.

It is still an additional object of the present invention to provide a metal matrix composite material which is stiffer and lighter than aluminum while being as hard as steel and extremely fracture resistant while also being extrudable and weldable, thus permitting the fabrication of extremely high strength, lightweight structural members at reasonable cost.

It is still an additional object of the present invention to provide a method for manufacturing an improved metal matrix composite material to result in a material having superior hardness, strength, and density characteristics while being extrudable and weldable for use in the manufacture of a variety of structural members which may be readily connected to one another such as in bicycle and other vehicle frames and components, engine components, aircraft parts, tooling, sporting equipment such as tennis rackets, badminton rackets, baseball bats, arrows, carabiner, golf club shafts and heads, hockey and lacrosse sticks, eyewear, automotive parts, computer hard disk substrates, electronic parts, furniture, medical equipment, battery housings, nuclear shielding, marine components, robots, carts and seats, gourmet cookware, toy casings, high-pressure containers, tank linings, and armor, for example.

DETAILED DESCRIPTION OF PREFERRED EMBODIMENTS

One preferred embodiment of the present invention uses aluminum alloy as a base material metal and boron carbide as the added ceramic material. In a preferred embodiment of manufacture the aluminum alloy is provided in the form of a metal powder which is blended with jet milled boron carbide particulates that have been processed and have certain chemical and particulate size attributes. The boron carbide is preferably at least 99.5% pure and has a 1–25 micron particle size with an average particle size of about 8.4 microns. Included in the boron carbide powder is 0.1–0.4% silicon, 0.05–0.4% iron, and 0.05–0.4% aluminum. Trace amounts of magnesium, titanium, and calcium may also be provided. Two exemplary semi-quantitative analyses of acceptable boron carbide powders for use in the present invention are shown hereinbelow in Tables 1–2.

TABLE 1

| | |
|---|---|
| B | 77.3% |
| Si | 0.37 |
| Mg | 0.0016 |
| Fe | 0.026 |
| Al | 0.18 |

TABLE 1-continued

| | |
|---|---|
| Cu | 0.0021 |
| Ti | 0.0088 |
| Ca | 0.0049 |
| other elements | (nil) |
| C, $O_2$ | (bal) |

TABLE 2

| | |
|---|---|
| B | 77.7% |
| Si | 0.14 |
| Mg | 0.0017 |
| Fe | 0.074 |
| Al | 0.13 |
| Cu | ND0.0002 |
| Ti | 0.017 |
| Ca | 0.0048 |
| other elements | (nil) |
| C, $O_2$ | (bal) |

The inclusion of small amounts of pure aluminum, silicon, and iron to the arc furnace during the production of boron carbide, such as by the reaction of boric acid and carbon, has been found to improve the boron carbide for use in this metal matrix composite. These elements are usually present in an amount less than 3.0° by weight. These metal elements do not go out of solution. They stay in the boron carbide and provide a chelating opportunity for the base material aluminum. These additional metals form an intermetallic chemical bond with the main metal alloy. However, it will be understood that the aforementioned inclusions of pure aluminum, silicon, and iron, may not be the only metals which can be used for the aforementioned purpose. By way of example, virtually any low temperature reacting metal that forms an intermetallic phase below the processing temperature of the metal matrix composite ingot would be usable in the present invention for the purpose indicated.

$Al_2O_3$ or SiC can also be added as reinforcement particulates which comprise between 0.01 and 40.0 volume percent of the metal matrix composite materials. The addition of these reinforcement particulates improve both the elasticity of modulus and the yield strength of the metal composite materials. In one embodiment of the invention, the reinforcement particulates are between 0.02 and 30 volume percent of metal matrix composite materials. In another preferred embodiment of the invention, the reinforcement particulates are between 0.05 and 10 volume percent of metal matrix composite materials. In a further preferred embodiment of the invention, the reinforcement particulates are between 0.1 and 5 volume percent of metal matrix composite materials.

The relative volume contribution of the boron carbide powder and base material metal powder is 0.1–50% of the former and 50–99.9% of the latter depending upon the specific characteristics desired for the finished product. Several typical formulations are as follows:

EXAMPLE 1

A metal matrix composite of aluminum alloy 6061 base metal material and 20 weight % boron carbide. This composite material is extrudable and exhibits a tensile strength of 65.3 kpsi and a yield strength of 59.8 kpsi. It is useful for structural components for transportation vehicles and computer discs. It has stiffness and strength.

EXAMPLE 2

A metal matrix composite of aluminum alloy 6061 base metal material and 25 weight % boron carbide. This composite material is extrudable and exhibits a tensile strength of 71.9 kpsi and a yield strength of 62.6 kpsi. This formulation is useful for brake discs and marine castings. It has corrosion resistance and wearability.

EXAMPLE 3

A metal matrix composite of aluminum alloy 6061 base metal material and 30 weight % boron carbide. This composite material is extrudable and exhibits a tensile strength of 62.3 kpsi and a yield strength of 58.4 kpsi. This formulation may be used for structural stiffness for marine applications or nuclear shielding since it has strength and corrosion resistance.

EXAMPLE 4

A metal matrix composite containing aluminum alloy 7091 base metal material and 20 weight % boron carbide. This composite material exhibits a tensile strength of 98.6 kpsi, a yield strength of 89.2 kpsi, and is extrudable. This composition has utility for spacecraft and satellites. It has low thermal expansion and high tensile strength.

EXAMPLE 5

A metal matrix composite containing aluminum alloy 7091 base metal material and 30 weight % boron carbide. This composite material exhibits a tensile strength of 107.9 kpsi, a yield strength of 96.4 kpsi, and is extrudable. The material is useful for containers for high pressure and corrosive materials. The material has high strength and corrosion resistance.

EXAMPLE 6

A matrix alloy composite of aluminum alloy 7093 conforms to the percentages by weight shown in Table 3, determined by inductively coupled plasma (ISP) or atomic absorption (AA) techniques.

The matrix alloy composite is reinforced by the addition of boron carbide particles which are between 1 and 25 microns in size. The boron carbide particles are uniformly dispersed throughout the aluminum matrix of the extruded products. The Reinforcement Volume Fraction of the boron carbide particles is 0.15±0.02 by volume, or 0.165±0.022 by weight using 2.80 g/cc for the density of the matrix alloy and 2.52 for the density of boron carbide, determined in accordance with ASTM D 3553.

TABLE 3

| Composition of Matrix Alloy | | |
|---|---|---|
| Element | Minimum | Maximum |
| Silicon | | 0.12 |
| Iron | | 0.15 |
| Copper | 1.10 | 1.90 |
| Manganese | | 0.10 |
| Magnesium | 2.00 | 3.00 |
| Chromium | | 0.10 |
| Nickel | | 0.16 |
| Zinc | 8.30 | 9.70 |
| Titanium | | 0.20 |
| Oxygen | 0.05 | 0.50 |
| Zirconium | | 0.20 |
| Others, Each | | 0.05 |
| Others, Total | | 0.15 |
| Aluminum | | Remainder |

Solution heat treatment is performed as follows: Heat the mixture of Al and $B_4C$ powders to 880–920° F. (470–495°

C.). Hold at temperature for a time commensurate with product thickness, with a minimum of 1 hours. Rapidly cool in a cold water or water-glycol(not more than 15% by volume glycol) solution. After drying, precipitation heat treat by heating to 240–260° F. (115–127° C.) and hold at temperature for 18 to 24 hours. After quenching, perform straightening before aging.

The extrusion was uniform in quality, temper and condition. The extrusion was clean, sound, smooth, and free from hard and soft spots, cracks, edge tears, internal voids and cavities, surface defects, kinks, damaged ends and other imperfections detrimental to usage of the extrusions.

The tensile properties of 7093 Alloy are shown in Table 4.

TABLE 4

Minimum Longitudinal Tensile Properties

| Particulate Concentration (±2 Vol %) => | 5% | 10% | 15% |
|---|---|---|---|
| Ultimate Strength, (kpsi) | 90 | 92 | 94 |
| Yield Strength, 0.2% Offset, (kpsi) | 83 | 85 | 87 |
| Elongation, 2 Inch Gauge Length | 5.0% | 3.5% | 2.5% |

Dimensions and properties are in inch/pound units and the Fahrenheit temperatures are primary; dimensions and properties in SI units and Celsius temperatures are shown as approximation equivalents of the primary units and are provided only for information.

The Young's Modulus of Elasticity for 7093 alloy is also measured and the data are listed in Table 5, determined by ASTM E 111.

TABLE 5

Young's Modulus of Elasticity Values.

| $B_4C$ particulate (±2 Vol %) | 5% | 10% | 15% |
|---|---|---|---|
| Modulus of Elasticity, (10 psi) | 11.0 | 12.5 | 14.0 |

Hardness is in the range of Rockwell B 85 to 100. Minimum tensile properties are based on extrusion ratios ranging from 20:1 to 150:1.

EXAMPLE 7

A matrix alloy composite of aluminum alloy 6092 conforms to the percentages by weight shown in Table 6, determined by inductively coupled plasma (ICP) or atomic absorption (AA) technique. The matrix alloy composite is reinforced by the addition of boron carbide particles which are between 1 and 25 microns in size. The boron carbide particles are uniformly dispersed throughout the aluminum matrix of the extruded products. The Reinforcement Volume Fraction of the boron carbide particles shall be 0.15±0.02 by volume, or 0.165±0.022 by weight using 2.80 g/cc for the density of the matrix alloy and 2.52 for the density of boron carbide, determined in accordance with ASTM D 3553.

TABLE 6

Aluminum Alloy Matrix Composition 6092 Alloy

| Element | Amount |
|---|---|
| Silicon | 0.60 to 1.00 |
| Iron | 0.50 Maximum |

TABLE 6-continued

Aluminum Alloy Matrix Composition 6092 Alloy

| Element | Amount |
|---|---|
| Copper | 0.60 to 1.00 |
| Manganese | 0.10 Maximum |
| Magnesium | 0.8 to 1.20 |
| Chromium | 0.10 Maximum |
| Nickel | 0.10 Maximum |
| Zinc | 0.25 Maximum |
| Titanium | 0.10 Maximum |
| Oxygen | 0.05 to 0.07 |
| Others, Each | 0.05 Maximum |
| Others, Total | 0.15 Maximum |
| Aluminum | Remainder |

Solution heat treatment is performed as follows: Heat the mixture of Al and $B_4C$ powders to 1020–1040° F. (550–560° C.) Hold at temperature for a time commensurate with product thickness, with a minimum of 1 hour. Rapidly cool in a cold water or water-glycol(not more than 15% by volume glycol) solution. After drying, precipitation heat treat by heating to 315–335° F. (157–170° C.) and hold at temperature for 4 to 6 hours. After quenching, perform straightening was aging.

The extrusion was uniform in quality, temper and condition. The extrusion was clean, sound, smooth, and free from hard and soft spots, cracks, edge tears, internal voids and cavities, surface defects, kinks, damaged ends and other imperfections detrimental to usage of the extrusions. The tensile properties of 6092 Alloy are shown in Table 7.

TABLE 7

Minimum Longitudinal Tensile Properties

| $B_4C$ Particulate (±2 Vol %) | 15% | 20% | 25% |
|---|---|---|---|
| Ultimate Strength | 65 kpsi | 70 kpsi | 75 kpsi |
| Yield Strength, 0.2% Offset | 54 kpsi | 56 kpsi | 58 kpsi |
| Elongation, 1 Inch Gauge Length | 3.5% | 3.0% | 2.5% |

The Young's Modulus of Elasticity for 6092 alloy is also measured for and the data are contained in Table 8, determined by ASTM E 111.

TABLE 8

Young's Modulus Elasticity Values

| $B_4C$ Particulate (±2 Vol %) | 15% | 20% | 25% |
|---|---|---|---|
| Modulus of Elasticity, (10 psi) | 13.5 | 14.5 | 15.5 |

EXAMPLE 8

Figure 2:
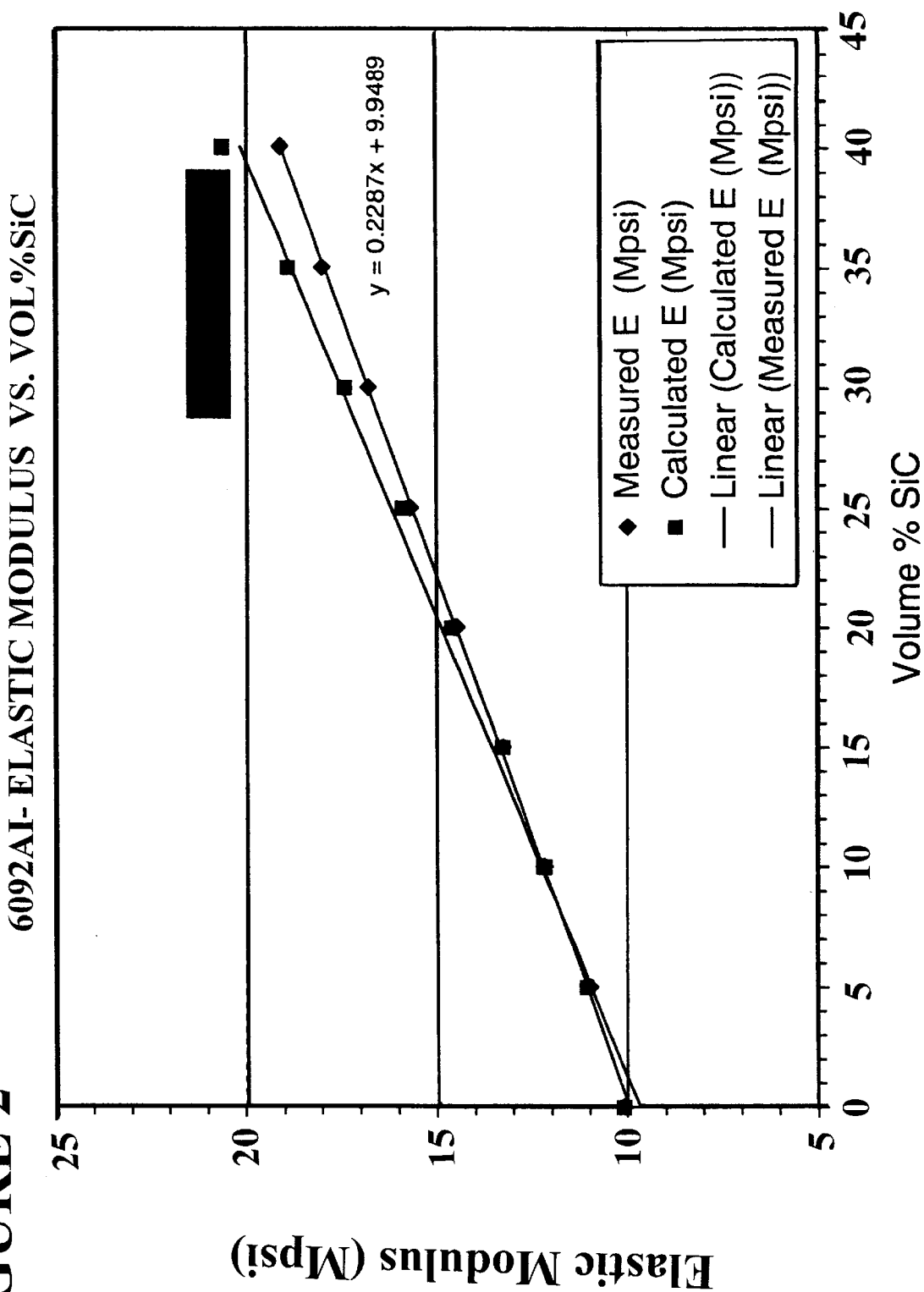
FIG. 2 is a graph of elastic modulus (MPsi) of matrix alloy composites of 6092 aluminum alloy as a function of SiC content.

Matrix alloy composites of aluminum alloy 6092 are reinforced by up to 40% of SiC particles. The Young's Modulus Elasticity Values as a function of volume percentage of SiC are measured. See FIGS. 1 and 2. The Young's Modulus Elasticity Values as a function of volume percentage of SiC are also calculated for matrix composite alloys containing 40 to 50% SiC using empirical equations. The measured and calculated Modulus Elasticity Values for SiC reinforced metal matrix composites are listed in Tables 9 and 10. The Modulus Elasticity Values in FIG. 1 and Table 9 have a unit of Giga-Pascal (Gpa) which equals $0.99 \times 10^4$ kg/cm². The Modulus Elasticity Values in FIG. 2 and Table 10 have a unit of Mpsi which equals $7.03 \times 10^4$ kg/cm.

TABLE 9

Elasticity Calculations & Measurements for
6092/SiC/0–40 vol %
E(6092Al) = 69.4 GPa  E(SiC) = 430 Gpa

| Volume % | Measured E (GPa) | Calculated E (GPa) |
| --- | --- | --- |
| 0 | 68.3 | 69.6 |
| 5 | 76.0 | 76.6 |
| 10 | 84.0 | 84.1 |
| 15 | 91.9 | 92.0 |
| 20 | 99.9 | 100.6 |
| 25 | 107.9 | 109.7 |
| 30 | 115.9 | 120.0 |
| 35 | 123.9 | 130.2 |
| 40 | 131.9 | 141.8 |

TABLE 10

Elasticity Calculations & Measurements for
6092/SiC/0–40 vol %
E(6092Al) = 10.1 Mpsi  E(SiC) = 62.4 Mpsi

| Volume % | Measured E (Mpsi) | Calculated E (Mpsi) |
| --- | --- | --- |
| 0 | 10.1 | 10.1 |
| 5 | 11.0 | 11.1 |
| 10 | 12.2 | 12.2 |
| 15 | 13.3 | 13.3 |
| 20 | 14.5 | 14.6 |
| 25 | 15.7 | 15.9 |
| 30 | 16.8 | 17.4 |
| 35 | 18.0 | 18.9 |
| 40 | 19.1 | 20.6 |

EXAMPLE 9

Figure 3:
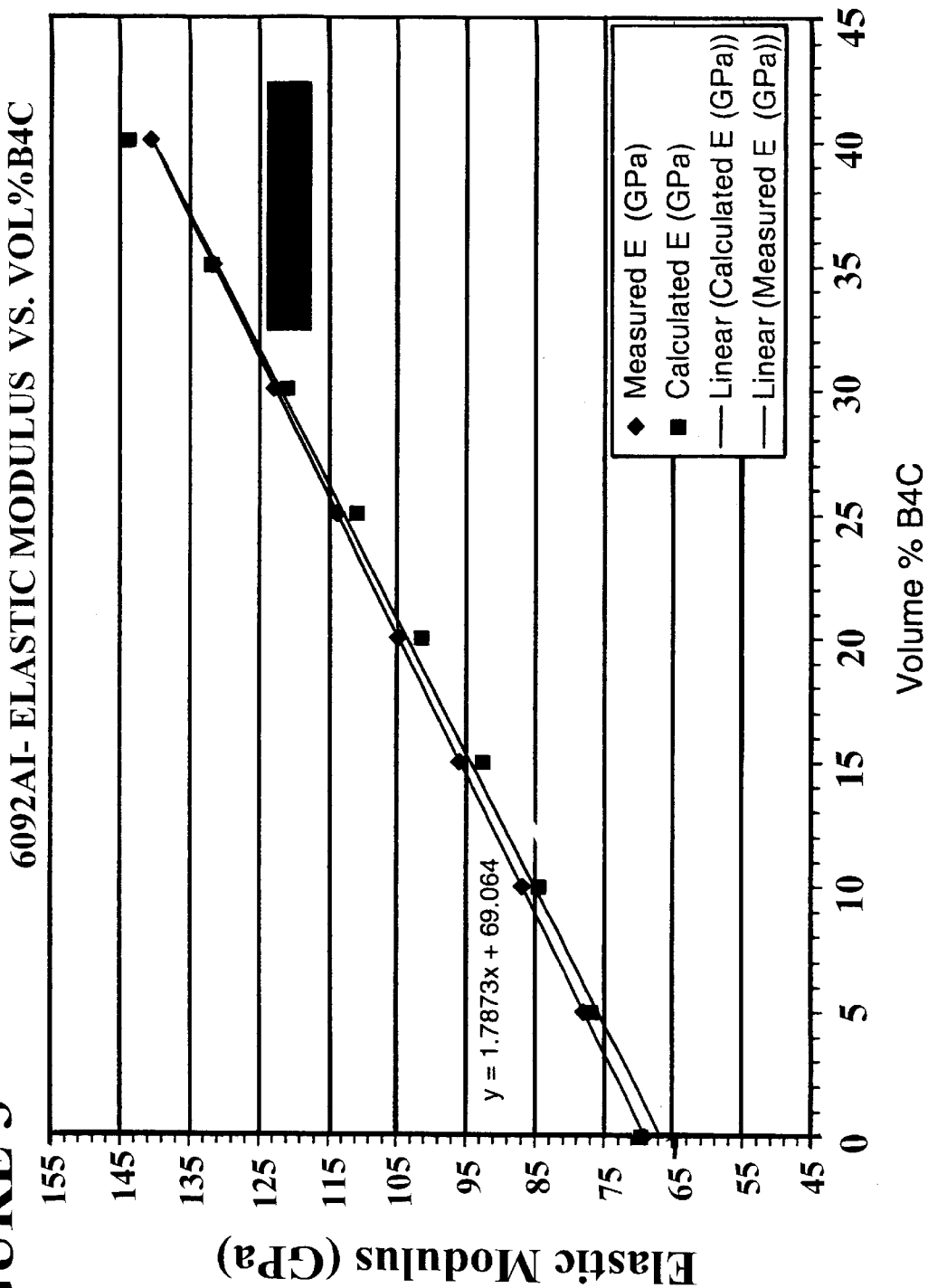
FIG. 3 is a graph of elastic modulus (GPa) of matrix alloy composites of 6092 aluminum alloy as a function of $B_4C$ content.
Figure 4:
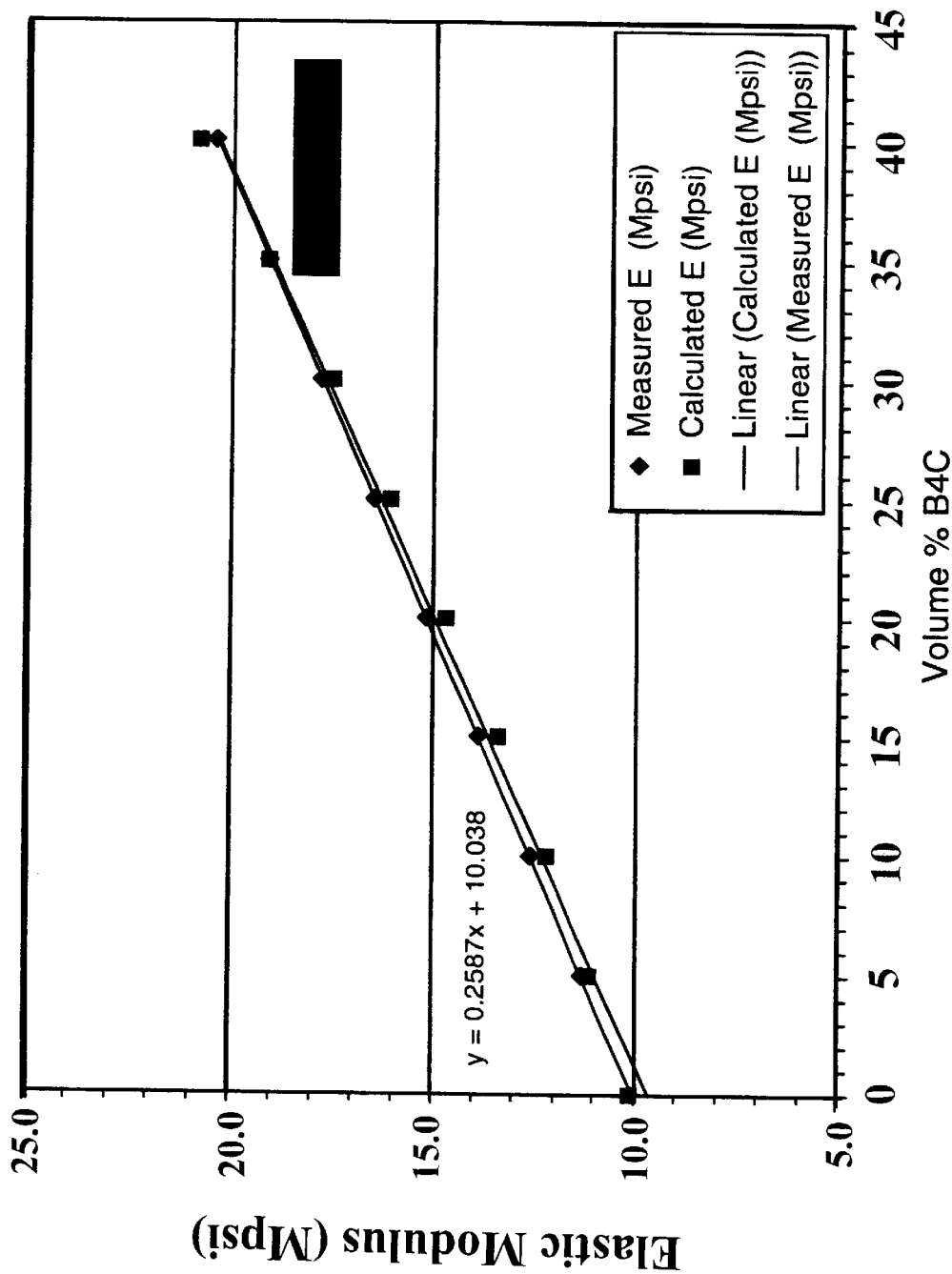
FIG. 4 is a graph of elastic modulus (MPsi) of matrix alloy composites of 6092 aluminum alloy as a function of $B_4C$ content.

Matrix alloy composites of aluminum alloy 6092 are reinforced by up to 40% of $B_4C$ particles. The Young's Modulus Elasticity Values as a function of volume percentage of $B_4C$ are measured. See FIGS. 3 and 4. The Young's Modulus Elasticity Values as a function of volume percentage of $B_4C$ are also calculated for matrix composite alloys containing 40 to 50% $B_4C$ using empirical equations. The measured and calculated Modulus Elasticity Values for $B_4C$ reinforced metal matrix composites are listed in Tables 11 and 12. The Modulus Elasticity Values in FIG. 3 and Table 11 have a unit of Giga-Pascal (Gpa) which equals $0.99 \times 10^4$ kg/cm$^2$. The Modulus Elasticity Values in FIG. 4 and Table 12 have a unit of Mpsi which equals $7.03 \times 10^4$ kg/cm.

TABLE 11

Elasticity Calculations & Measurements for
6092/B$_4$C/0–40 vol %
E(6092Al) = 69.4 GPa  E(B$_4$C) = 450 GPa

| Volume % | Measured E (GPa) | Calculated E (GPa) |
| --- | --- | --- |
| 0 | 69.1 | 69.6 |
| 5 | 78 | 76.8 |
| 10 | 86.9 | 84.4 |
| 15 | 95.9 | 92.5 |
| 20 | 104.8 | 101.3 |
| 25 | 113.7 | 110.7 |
| 30 | 122.7 | 120.8 |
| 35 | 131.6 | 131.8 |
| 40 | 140.6 | 143.7 |

TABLE 12

Elasticity Calculations & Measurements for
6092/B$_4$C/0–40 vol %
E(6092Al) = 10.1 Mpsi  E(B$_4$C) = 65.3 Mpsi

| Volume % | Measured E (GPa) | Calculated E (GPa) |
| --- | --- | --- |
| 0 | 10.1 | 10.1 |
| 5 | 11.3 | 11.1 |
| 10 | 12.6 | 12.2 |
| 15 | 13.9 | 13.4 |
| 20 | 15.2 | 14.7 |
| 25 | 16.5 | 16.1 |
| 30 | 17.8 | 17.5 |
| 35 | 19.1 | 19.1 |
| 40 | 20.4 | 20.8 |

EXAMPLE 10

Figure 5:
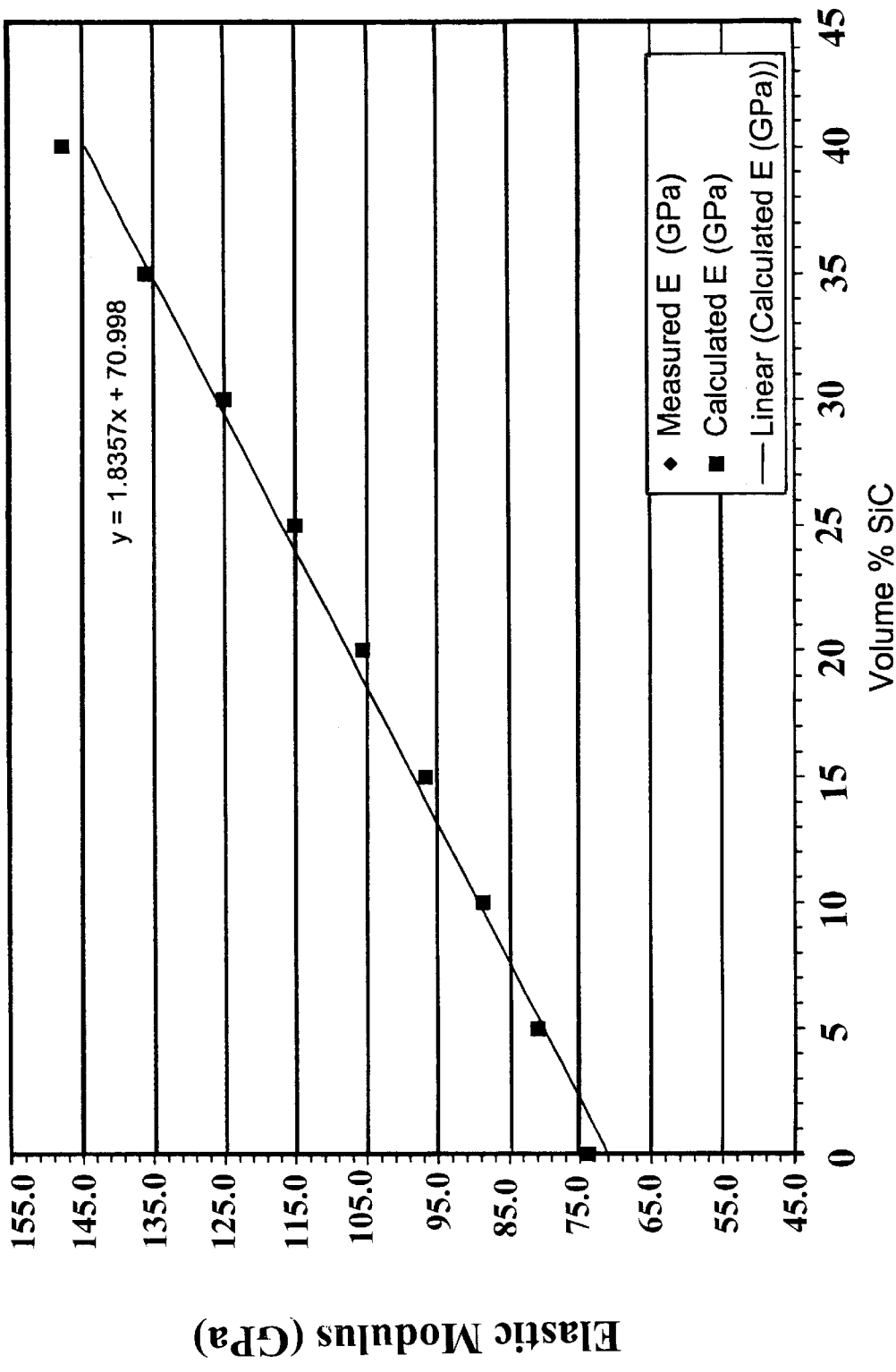
FIG. 5 is a graph of elastic modulus (GPa) of matrix alloy composites of 7093 aluminum alloy as a function of SiC content.
Figure 6:
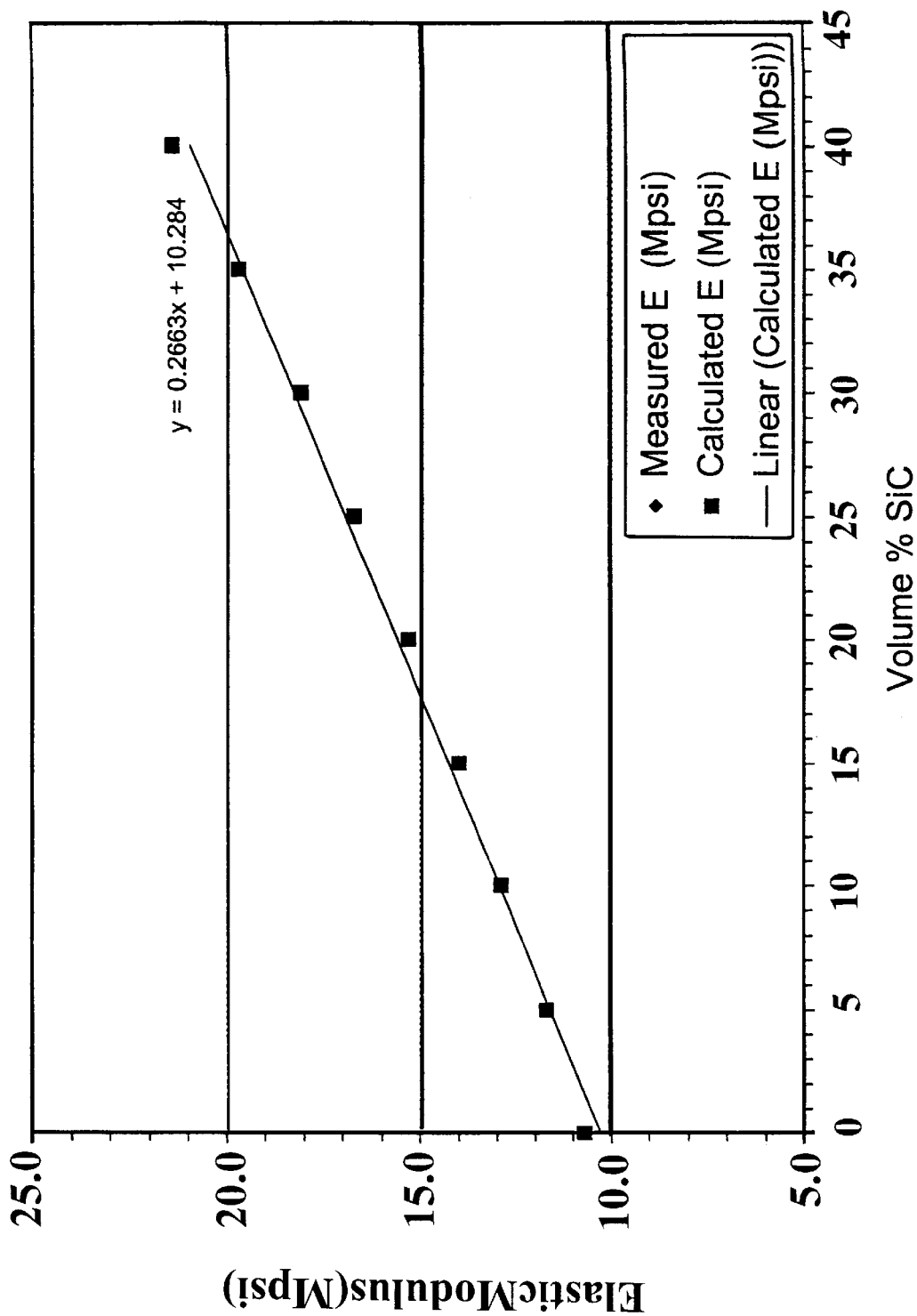
FIG. 6 is a graph of elastic modulus (MPsi) of matrix alloy composites of 7093 aluminum alloy as a function of SiC content.

Matrix alloy composites of aluminum alloy 7093 are reinforced by up to 40% of SiC particles. The Young's Modulus Elasticity Values as a function of volume percentage of SiC are calculated. See FIGS. 5 and 6. The Young's Modulus Elasticity Values as a function of volume percentage of SiC are also calculated for matrix composite alloys containing 40 to 50% SiC using empirical equations. The calculated Modulus Elasticity Values for SiC reinforced metal matrix composites are listed in Tables 13 and 14. The Modulus Elasticity Values in FIG. 5 and Table 13 have a unit of Giga-Pascal (Gpa) which equals $0.99 \times 10^4$ kg/cm$^2$. The Modulus Elasticity Values in FIG. 6 and Table 14 have a unit of Mpsi which equals $7.03 \times 10^4$ kg/cm$^2$.

TABLE 13

Elasticity Calculations & Measurements for
7093/SiC/0–40 vol %
E(7093Al) = 73.8 Gpa  E(SiC) = 430 GPa

| Volume % | Measured E (GPa) | Calculated E (GPa) |
| --- | --- | --- |
| 0 |  | 73.8 |
| 5 |  | 81.0 |
| 10 |  | 88.7 |
| 15 |  | 96.8 |
| 20 |  | 105.6 |
| 25 |  | 115.0 |
| 30 |  | 125.0 |
| 35 |  | 135.9 |
| 40 |  | 147.6 |

TABLE 14

Elasticity Calculations & Measurements for
7093/SiC/0–40 vol %
E(7093Al) = 10.7 Mpsi  E(SiC) = 62.4 Mpsi

| Volume % | Measured E (Mpsi) | Calculated E (Mpsi) |
| --- | --- | --- |
| 0 |  | 10.7 |
| 5 |  | 11.7 |
| 10 |  | 12.9 |
| 15 |  | 14.0 |
| 20 |  | 15.3 |
| 25 |  | 16.7 |
| 30 |  | 18.1 |
| 35 |  | 19.7 |
| 40 |  | 21.4 |

EXAMPLE 11

Figure 7:
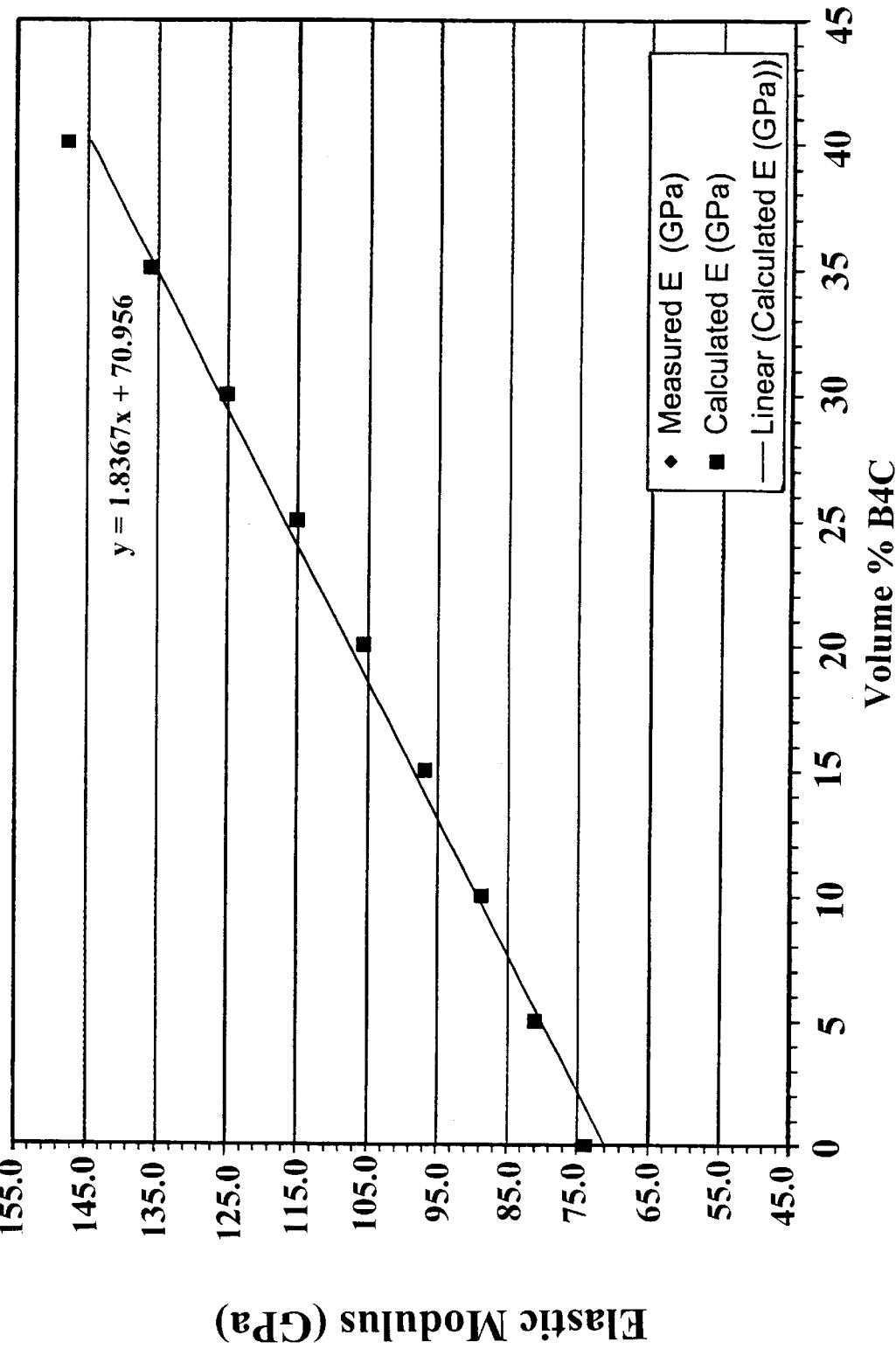
FIG. 7 is a graph of elastic modulus (GPa) of matrix alloy composites of 7093 aluminum alloy as a function of $B_4C$ content.
Figure 8:
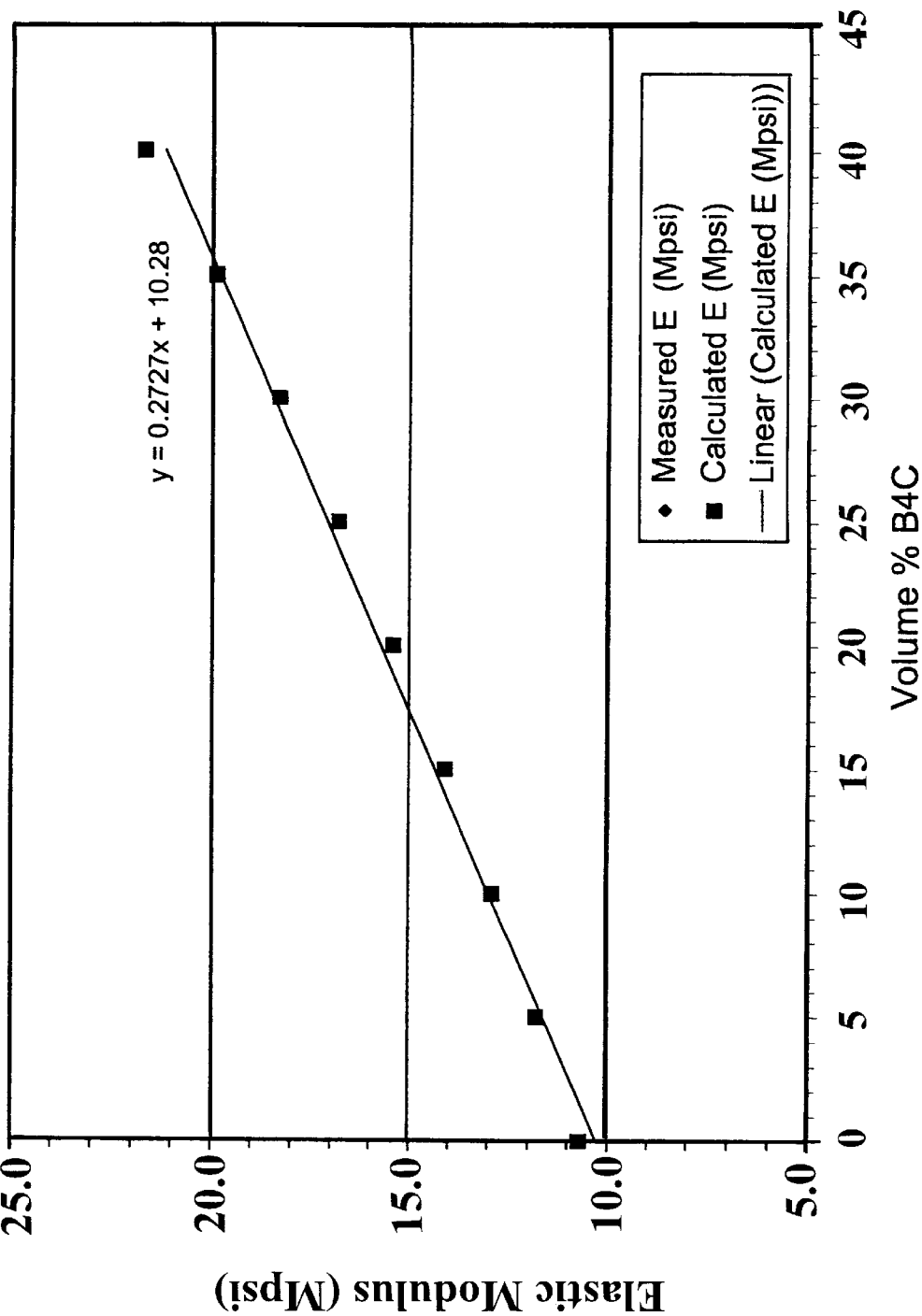
FIG. 8 is a graph of elastic modulus (MPsi) of matrix alloy composites of 7093 aluminum alloy as a function of $B_4C$ content.
Figure 9:
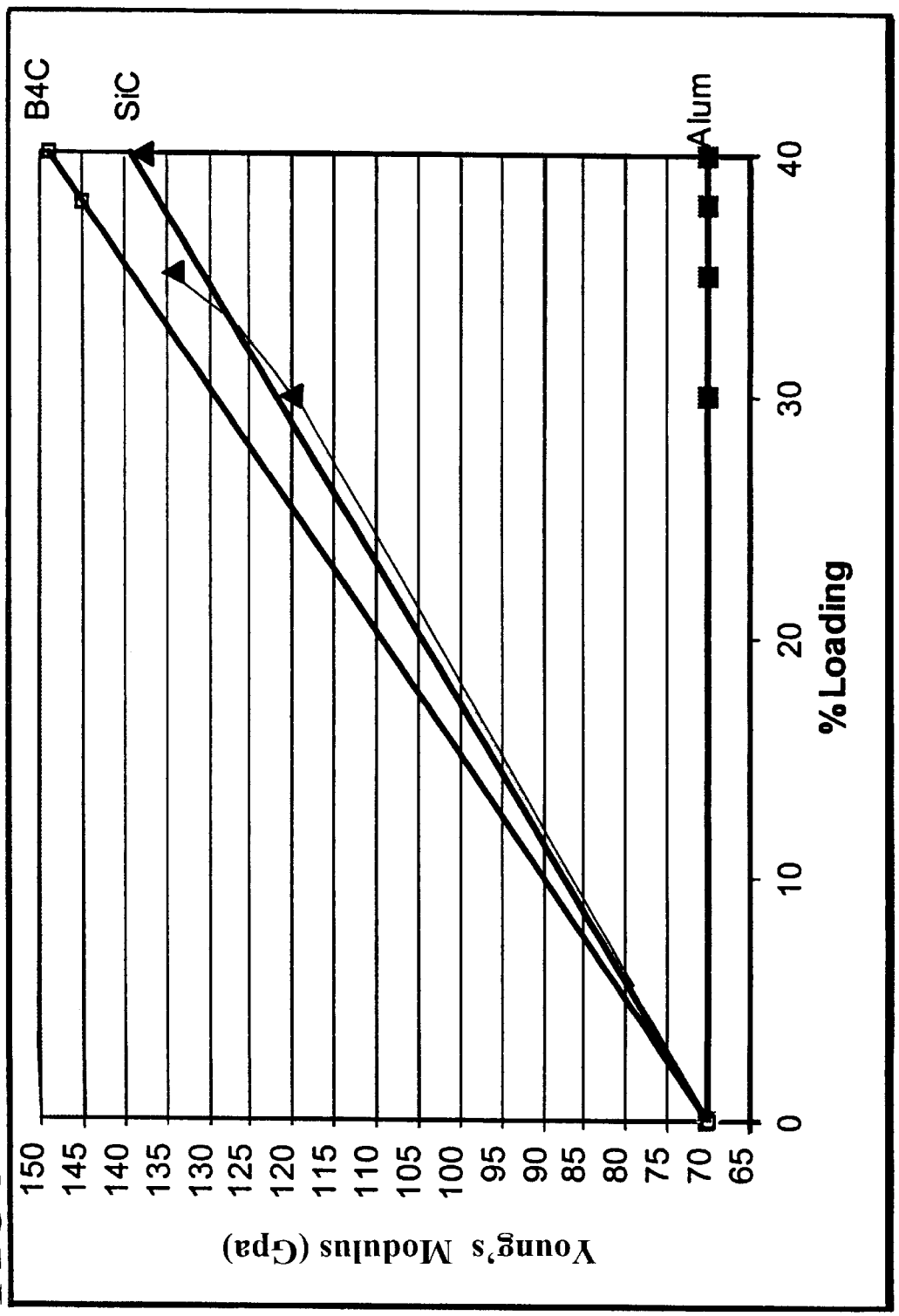
FIG. 9 is a graph of modulus of metal matrix composite against % loading.
Figure 10:
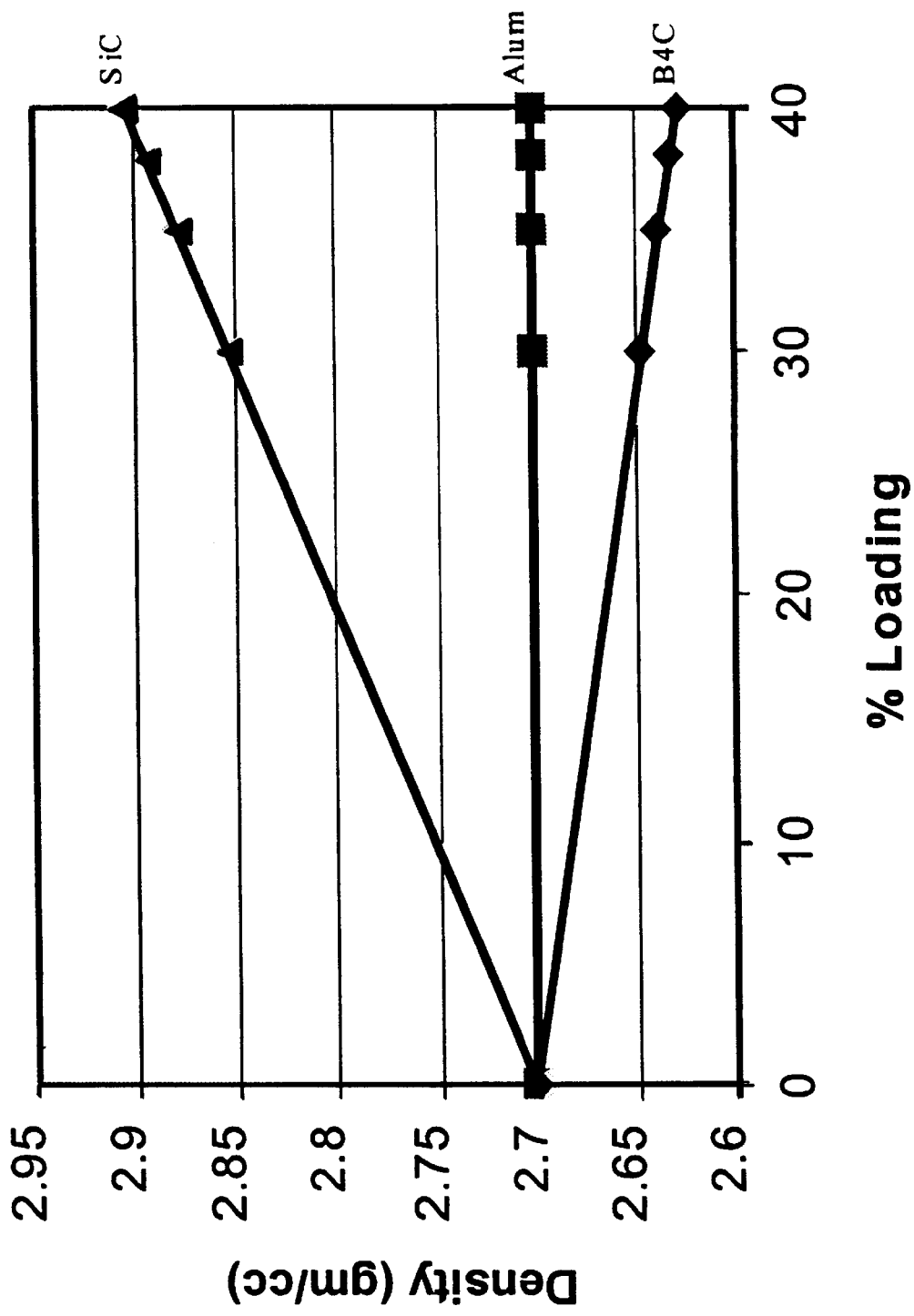
FIG. 10 is the graph of density of metal matrix against % loading.
Figure 11:
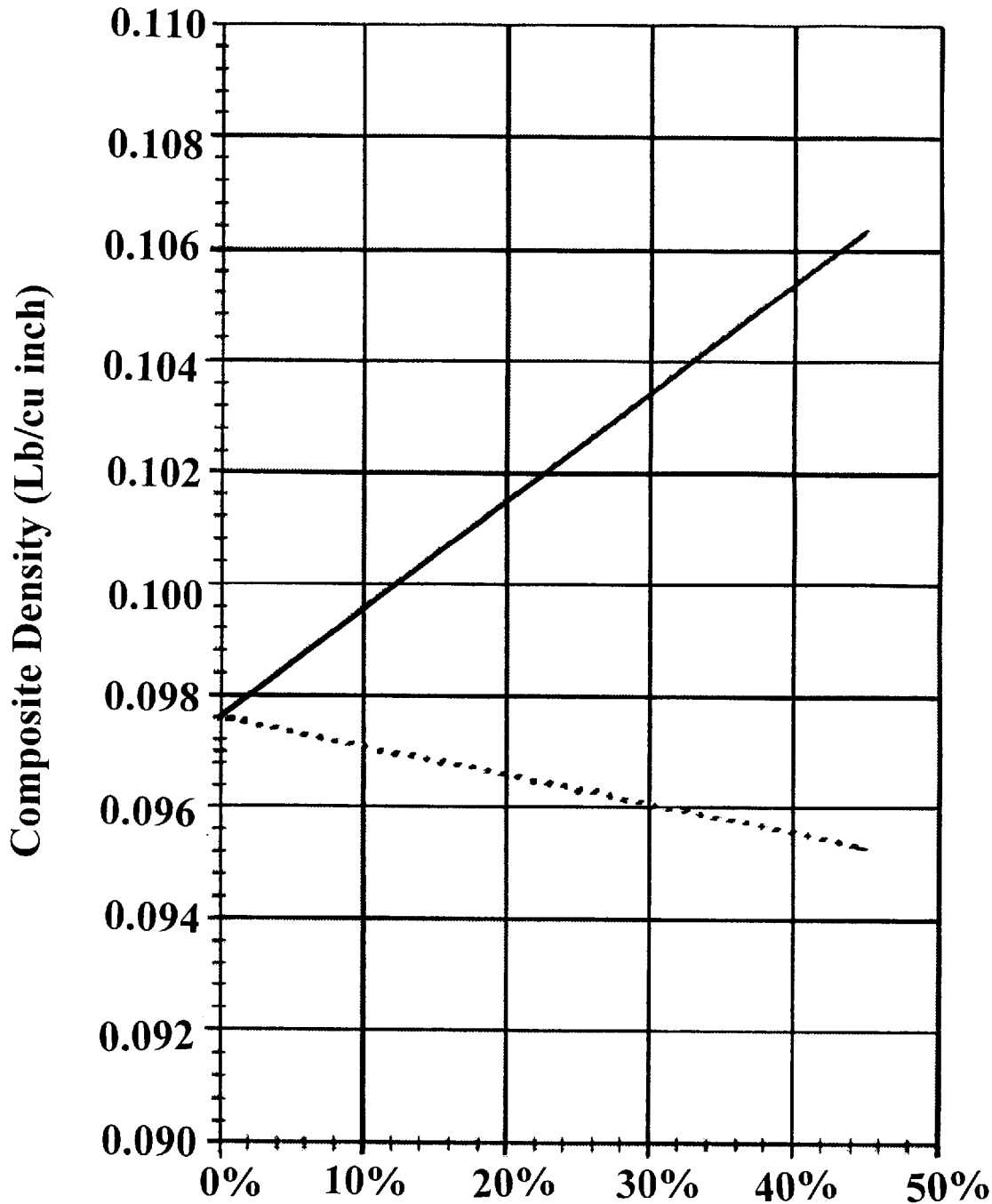
FIG. 11 is a graph of composite density as a function of volume % of SiC or $B_4C$.
Figure 12:
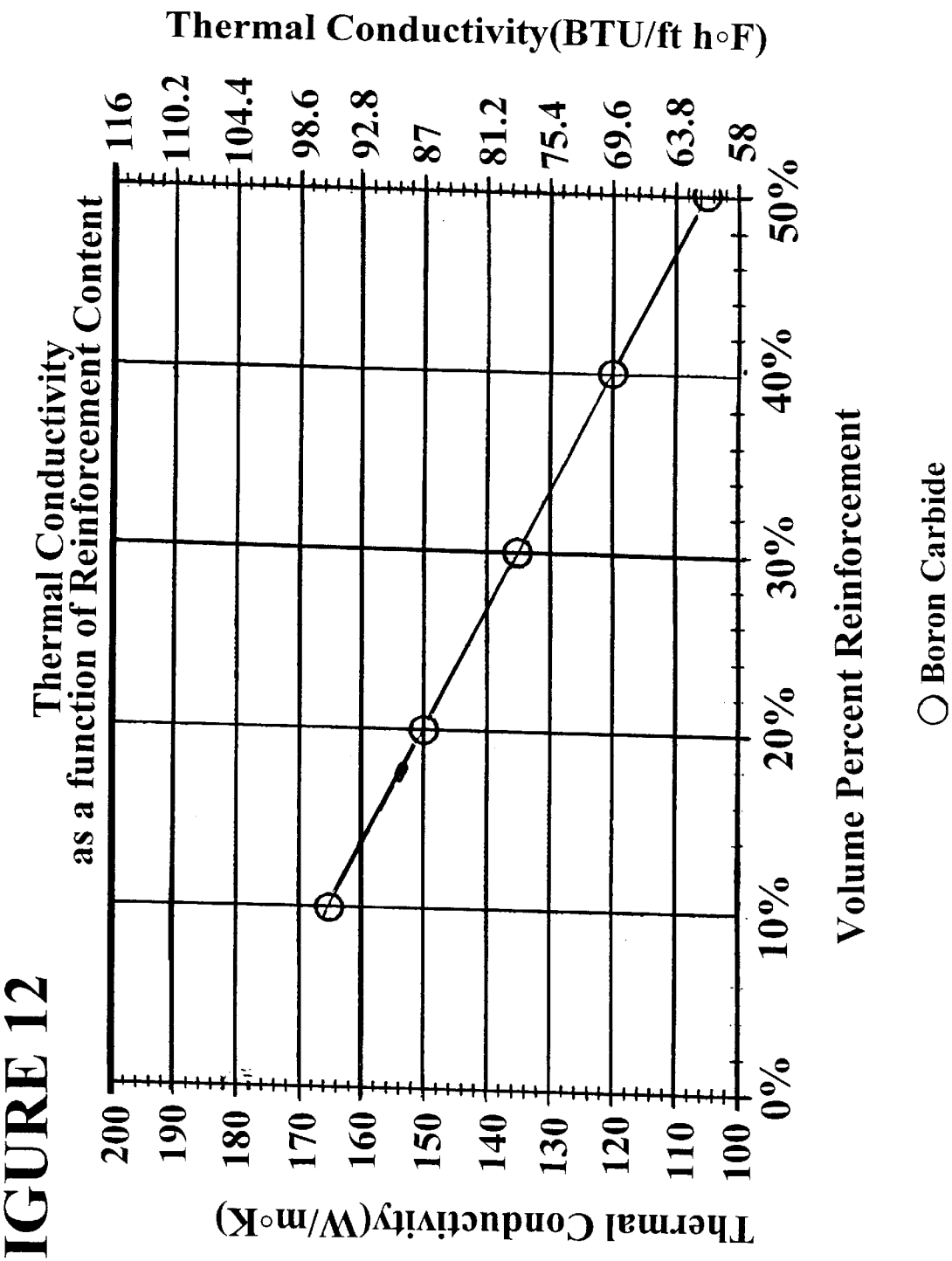
FIG. 12 is a graph of thermal conductivity of the composites as a function of reinforcement content.
Figure 13:
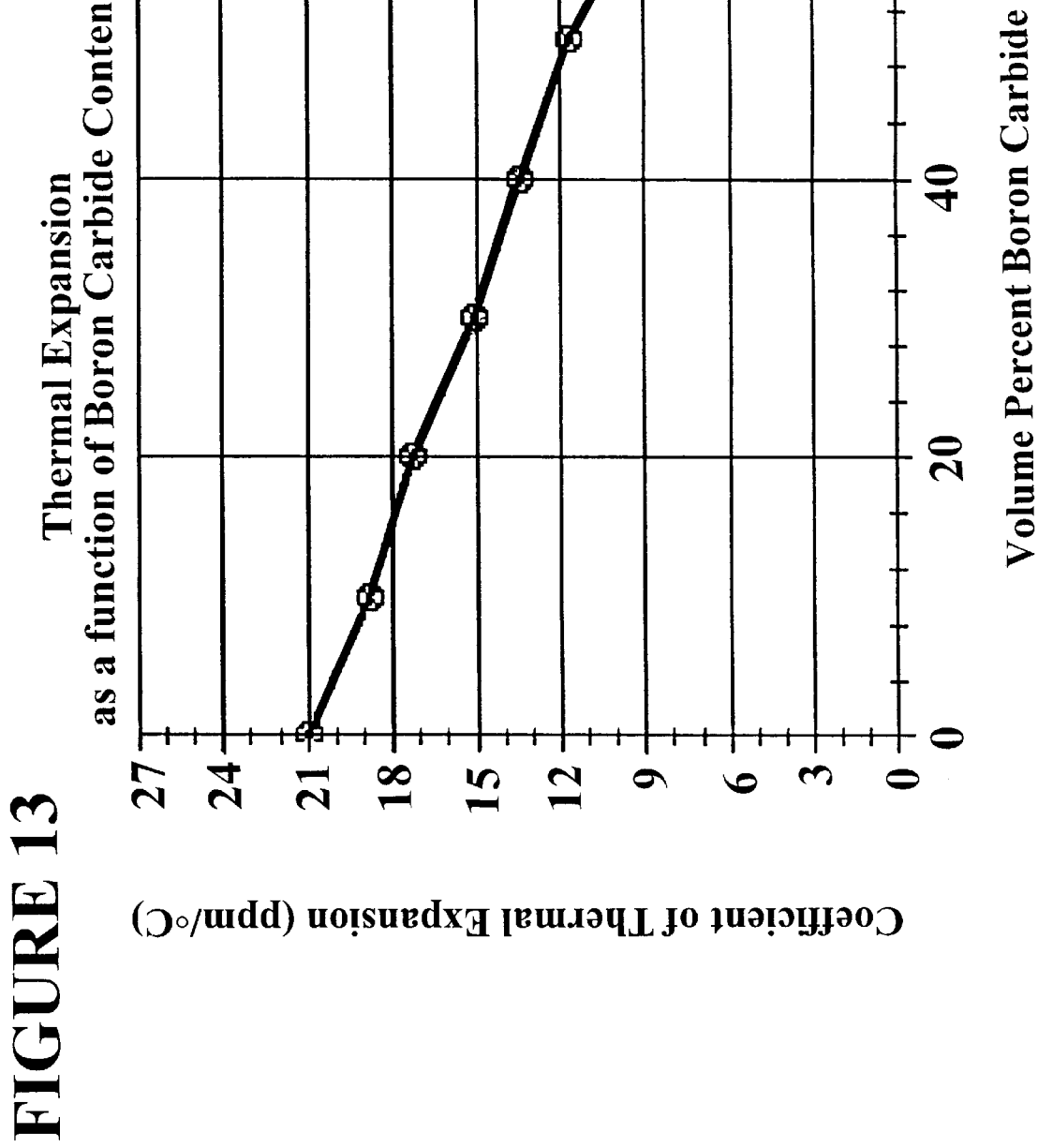
FIG. 13 is a graph of thermal expansion of the composites as a funtion of $B_4C$ content.

Matrix alloy composites of aluminum alloy 7093 are reinforced by up to 40% of $B_4C$ particles. The Young's Modulus Elasticity Values as a function of volume percentage of $B_4C$ are calculated. See FIGS. 7 and 8. The Young's Modulus Elasticity Values as a function of volume percentage of $B_4C$ are also calculated for matrix composite alloys containing 40 to 50% $B_4C$ using empirical equations. The calculated Modulus Elasticity Values for $B_4C$ reinforced metal matrix composites are listed in Tables 15 and 16. The Modulus Elasticity Values in FIG. 7 and Table 15 have a unit of Giga-Pascal (Gpa) which equals $0.99 \times 10^4$ $kg/cm^2$. The Modulus Elasticity Values in FIG. 8 and Table 16 have a unit of Mpsi which equals $7.03 \times 10^4$ kg/cm.

TABLE 15

Elasticity Calculations & Measurements for 7093/$B_4$C/0–40 vol %
E(7093Al) = 73.8 GPa E($B_4$C) = 450 GPa

| Volume % | Measured E (GPa) | Calculated E (GPa) |
|---|---|---|
| 0 | | 73.8 |
| 5 | | 81.1 |
| 10 | | 88.6 |
| 15 | | 96.7 |
| 20 | | 105.5 |
| 25 | | 114.9 |
| 30 | | 125.0 |
| 35 | | 135.9 |
| 40 | | 147.7 |

TABLE 16

Elasticity Calculations & Measurements for 7093/$B_4$C/0–40 vol %
E(7093Al) = 10.7 Mpsi E($B_4$C) = 65.3 Mpsi

| Volume % | Measured E (MPsi) | Calculated E (MPsi) |
|---|---|---|
| 0 | | 10.7 |
| 5 | | 11.8 |
| 10 | | 12.9 |
| 15 | | 14.1 |
| 20 | | 15.4 |
| 25 | | 16.8 |
| 30 | | 18.3 |
| 35 | | 19.9 |
| 40 | | 21.7 |

As shown above, this invention provides an extrudable and weldable matrix alloy composite comprising: a) a base material metal of about 50 to 99.9% by weight, b) boron carbide of about 0.1 to 50% by weight, the boron carbide being substantially homogeneously distributed among the metal, forming close grain boundaries therewith; and c) less than about 3.0% by weight of at least one metal having an intermetallic phase temperature lower than the melting point of the base material metal, the metal being included with the boron carbide during its production to provide a chelating opportunity for the base material metal.

In one embodiment of the extrudable and weldable matrix alloy material, a reinforcement agent of up to about 30% by weight is added.

In another embodiment of the extrudable and weldable matrix alloy composite, the reinforcement agent is between 0.5 and 5% by weight.

In another embodiment of the extrudable and weldable matrix alloy composite, the base material metal is selected from the group comprising aluminum, titanium and alloys thereof.

In another embodiment of the extrudable and weldable matrix composite, the aluminum alloy comprises aluminum alloy 6092 or aluminum alloy 7093.

In another embodiment of the extrudable and weldable matrix alloy composite, the composite has an elasticity modulus value of between 10 to 21 Mpsi.

In another embodiment of the extrudable and weldable matrix alloy composite, the composite has an elasticity modulus value of between 14 to 18 Mpsi.

In another embodiment of the extrudable and weldable matrix alloy composite, the $B_4C$ content is about 0.1 to 9.5 percent by weight.

In another embodiment of the extrudable and weldable matrix alloy composite, the $B_4C$ content is about 35 to 50 percent by weight.

In another embodiment of the extrudable and weldable matrix alloy composite, the reinforcement agent comprises aluminum oxide or silicon carbide.

In another embodiment of the extrudable and weldable matrix alloy composite, the composite has a density of about 2.40 to 2.80 grams per cubic centimeter.

In another embodiment of the extrudable and weldable matrix alloy composite, the composite has a tensile strength of about 10–110 kpsi.

In another embodiment of the extrudable and weldable matrix alloy composite, the composite has a tensile strength of about 10–90 kpsi.

In another embodiment of the extrudable and weldable matrix alloy composite, the composite has a tensile strength of about 10–70 kpsi.

In another embodiment of the extrudable and weldable matrix alloy composite, the composite has a tensile strength of about 10–60 kpsi.

In another embodiment of the extrudable and weldable matrix alloy composite, the composite has a tensile strength of about 10–40 kpsi.

In another embodiment of the extrudable and weldable matrix alloy composite, the composite has a tensile strength of about 10–20 kpsi.

In another embodiment of the extrudable and weldable matrix alloy composite, the composite has a tensile strength of about 60–110 kpsi.

In another embodiment of the extrudable and weldable matrix alloy composite, the composite has a tensile strength of about 80–100 kpsi.

In yet another embodiment of the extrudable and weldable matrix alloy composite, the composite has a thermal conductivity of about 60 to 170 W/m° K.

In a further embodiment of the extrudable and weldable matrix alloy composite, the composite has a thermal expansion coefficient of about 9 to 21 ppm/° C.

This invention also provides an extrudable and weldable matrix alloy composite comprising: a) a base material metal of about 50 to 99.9% by weight, b) silicon carbide of about 0.1 to 50% by weight, the silicon carbide being substantially homogeneously distributed among the metal, forming close grain boundaries therewith; and c) less than about 3.0% by weight of at least one metal having an intermetallic phase temperature lower than the melting point of the base material metal, the metal being included with the boron carbide during its production to provide a chelating opportunity for the base material metal.

In one embodiment of the extrudable and weldable matrix alloy composite, a reinforcement agent of up to about 30% by weight is added.

In another embodiment of the extrudable and weldable matrix alloy composite, the reinforcement agent is between 0.5 and 5% by weight.

In another embodiment of the extrudable and weldable matrix alloy composite, the base material metal is selected from the group comprising aluminum, titanium and alloys thereof.

In another embodiment of the extrudable and weldable matrix composite, the aluminum alloy comprises aluminum alloy 6092 or aluminum alloy 7093.

In another embodiment of the extrudable and weldable matrix alloy composite, the composite has an elasticity modulus value of between 10 to 21 Mpsi.

In another embodiment of the extrudable and weldable matrix alloy composite, the composite has an elasticity modulus value of between 14 to 18 Mpsi.

In another embodiment of the extrudable and weldable matrix alloy composite, the reinforcement agent comprises aluminum oxide.

In another embodiment of the extrudable and weldable matrix alloy composite, the composite has a density of about 2.60 to 3.00 grams per cubic centimeter.

In another embodiment of the extrudable and weldable matrix alloy composite, the composite has a tensile strength of about 10–110 kpsi.

In another embodiment of the extrudable and weldable matrix alloy composite, the composite has a tensile strength of about 10–90 kpsi.

In another embodiment of the extrudable and weldable matrix alloy composite, the composite has a tensile strength of about 10–60 kpsi.

In another embodiment of the extrudable and weldable matrix alloy composite, the composite has a tensile strength of about 10–40 kpsi.

In yet another embodiment of the extrudable and weldable matrix alloy composite, the composite has a tensile strength of about 10–20 kpsi.

In a further embodiment of the extrudable and weldable matrix alloy composite, the composite has a tensile strength of about 60–100 kpsi.

As used herein, the phrase "elasticity value" means the value of Young's Modulus of Elasticity.

In preparing the matrix alloy composites, after the boron carbide has been jet milled to the selected particulate size and with the aluminum alloy powder blended together in a double chamber "V" blender, for two and one-half hours at 20 to 30 RPM in an inert gas, the powders are degassed at 200 degrees Centigrade for one hour in a vacuum of 5 to 8 Torr and then placed in a latex bag and isopressed at 65,000 psi. The isopress bag resembles the shape of the ingot that is to be extruded. The latex bag is degassed and clamped off. The maximum pressure is held for at least a one minute soak. The resulting ingots are removed from the bag and placed into a vacuum furnace to undergo a sintering cycle in accordance with the following process.

First, the ingots are heated from room temperature to 300 degrees Centigrade over a twenty minute ramp period during which time binder and water are burned off. The ingots are then heated to 450 degrees Centigrade over a fifteen minute ramp period during which the remaining binder is burned off. The ingots are then heated to 625 degrees Centigrade over a forty minute ramp period during which the temperature increases accordingly. At 625 degrees Centigrade the ingot is held and soaked at that temperature for 45 minutes during which close grain boundaries are formed. The ingot is then cooled from 625 degrees Centigrade to 450 degrees Centigrade over a twenty minute period by means of a nitrogen gas backfill. Finally, the ingots are cooled to room temperature at a rate not faster than 40 degrees Centigrade per minute again using nitrogen gas. The ingots are then turned down by a metal lathe to bring them into an extruding shape with a typical selected outer diameter of between 3½ and 7 inches to a tolerance of 15,000ths of an inch. The ingots are then available for extrusion.

Extruding the metal matrix composite of the present invention can be performed using a process which first involves preheating the ingots in a resistance furnace for a minimum period of one hour at 555 degrees Centigrade. This is normally done in two steps. First, the ingots are heated to 315 degrees Centigrade in a holding furnace and then heated to a higher temperature and held until the ingot temperature reaches 555 degrees Centigrade. The ingots are then loaded directly into a container or chamber from the furnace. The chamber temperature should preferably be 488 degrees Centigrade. The face pressure within the chamber depends upon the type of extrusion dimensions that are desired. Typically, the pressures used are 15–20% higher than extrusion pressures used for 6061 aluminum ingots. For example, for a 3½ inch outer diameter billet made of the metal matrix composite of the present invention, 3,500 psi peak (break out) pressure is typically used and results in an extruding pressure of about 3,000 psi. The speed of the extrusion could be an average of 15–30 feet per minute and the exit temperature should be 20 degrees Centigrade cooler than the container temperature. The speed of the ram used for the extrusion should run 3½ inches every minute on a typical 3½ inch outer diameter ingot.

Although the present invention may be extruded in conventional dies, it has been found that for maximum die insert life, a die bearing material made of titanium diboride is preferred. The titanium diboride die bearing material is preferably hot pressed and then electrodischarge machined to the appropriate size. A small amount of boron carbide may be used to increase the hardness of the die. Typically, the die is made of 99.5% pure titanium diboride in an amount equal to 92–98% by weight, the remaining fraction being 99.5% pure boron carbide having particulate sizes less than 10 microns. The hot press cycle for manufacture of the die bearing material is preferably done at 1,800 degrees Centigrade using a 3,500 psi pressure with the pressure and temperature maintained until a zero drop in ram travel is obtained.

The extruded metal matrix composite provides the greatest benefit if it is heat treated using a T6-type heat treatment which comprises two hours at 530 degrees Centigrade with a cold water quench and an artificial aging at 177 degrees Centigrade for ten hours. All welding, however, has to be accomplished before heat treatment is applied. Unlike other metal matrix composites which contain silicon carbide and aluminum oxide where welding can be a problem, the metal matrix composite of the present invention is readily weldable. Other metal matrix composites form aluminum carbides as brittle components of a weld. Aluminum carbides are formed from the chemical reaction of aluminum and silicon carbide. Because of the surface area of the aluminum oxide particulates and metal matrices, clumping and dewetting occurs. These brittle components and particulates clump together thereby greatly decreasing the strength of a weld body. The metal matrix composite of the present invention does not have these problems. The coated boron carbide particulates tend to flux and move into the weld pool which creates a very strong weld joint. Because boron carbide particulates have a melting point of 2,450 degrees Centigrade, the boron carbide is chemically inert at aluminum processing temperatures.

Depending upon the ratio of boron carbide to aluminum and also depending upon the particular aluminum alloy used as the base material metal, the resulting material has a density of less than 2.70 grams per cubic centimeter which is lower than aluminum 6061. One formulation has a density of 2.52 grams per cubic centimeter. The resulting material also has a tensile strength of 62–108 kpsi, a yield strength of 58–97 kpsi, a modulus of elasticity of from 14.25–14.50 Mpsi, and is extremely fracture resistant and more predictable than other composites. Furthermore, the resulting material of the present invention has a hardness which is comparable to that of titanium and chromoly steel, but a density which is roughly a third of steel and roughly 60% of titanium.

Some particular exemplary applications of the material of the inventions are as follows:

1) Discs used as substrates for hard drives in computer systems.
2) Extruded structural components for various transportation vehicles—e.g. bicycles, motorcycles, aircraft, military vehicles —including frames, interior floors and panels, handle bars, propulsion structures, flight control systems, fuel management systems and landing gear.
3) Cast structural components and auxiliary parts for various transportation vehicles—bicycles, motorcycles, aircraft, and auto water pumps, bicycle cranks, disc brakes, and landing gear.
4) Housings for batteries where light weight and corrosion resistance are important.
5) Housings for electronic "boxes" for numerous applications where weight, high impact strength, and low thermal expansion are considerations—e.g., stamped casings for cellular phones, notebook computers, portable electronics.
6) Extruded structural parts of sporting goods equipment, e.g., tennis rackets, badminton rackets, baseball bats, arrows, golf club shafts, eyeglasses, oars, hockey sticks, billiard cues, ping pong paddles, lacrosse sticks, racquet ball rackets and basketball stanchions.
7) Cast sporting goods components such as golf club shafts and heads, archery equipment, ball throwing equipment, camping equipment, exercise equipment, fishing reels, hiking and mountaineering accessories, skate trucks, locks, optical frames, rowing equipment, water skis and snowboards.
8) Spray coatings for thermal, abrasive, and other forms of protection.
9) Nuclear shielding applications.
10) Internal combustion engine components—engine blocks, pistons, rods, valves, camshafts, and crankshafts.
11) Marine applications for extruded and cast material— spars, turnbuckles, propellers, and portholes.
12) Robotics applications for extruded and cast material where light weight, strength and fatigue resistance are critical.
13) Substrates for high power electronic components.
14) Structures for carts, amusement rides, ski lifts, elevators, escalators, moving sidewalks, trams and other general people moving purposes.
15) Gourmet cookware, knives, and other consumer niche markets.
16) Casings and parts for toys.
17) Armor for vehicles, personal security.
18) High pressure containers; e.g. gas storage, power transformers.
19) Casings and bits for down-hole drilling assemblies in oil prospecting.
20) Large structures where weight and toughness is important—e.g., inner hulls for oil tanker ships.
21) Portable tools of all kinds, for industrial, commercial, medical and construction use, where light weight and toughness are paramount.
22) Medical applications—e.g. prosthesis, braces, medical instruments and tools, where strength and light weight are important.
23) Dental applications—drill bits.
24) Transducers—bases and other parts of sensors for temperature and other parameters.
25) Channels, attenuators, combiners and other components of microwave networks and transmission systems.
26) Structures for spacecraft and satellites where low thermal expansion and light weight are key features.

Although described herein are preferred embodiments of the material composition and method of fabrication of the present invention, the invention may have other applications and embodiments. Such modifications as are within the knowledge of those skilled in the art are encompassed by the spirit and scope of the invention.

I claim:

1. An extrudable and weldable matrix alloy composite comprising:
   a) a base material metal of about 50 to 99.9% by weight,
   b) boron carbide of about 0.1 to 50% by weight, the boron carbide being substantially homogeneously distributed among the metal, forming close grain boundaries therewith; and
   c) less than about 3.0% by weight of at least one metal having an intermetallic phase temperature lower than the melting point of the base material metal, the metal being included with the boron carbide during its production to provide a chelating opportunity for the base material metal.

2. The extrudable and weldable matrix alloy composite of claim 1, further comprising an reinforcement agent of up to 30% by weight.

3. The extrudable and weldable matrix alloy composite of claim 2 wherein the reinforcement agent is between 0.5 and 5% by weight.

4. The extrudable and weldable matrix alloy composite of claim 1, wherein the base material metal is selected from the group comprising aluminum, titanium and alloys thereof.

5. The extrudable and weldable matrix alloy composite of claim 4, wherein the aluminum alloy comprises aluminum alloy 6092 or aluminum alloy 7093.

6. The extrudable and weldable matrix alloy composite of claim 1, wherein the composite has an elasticity modulus value of between 10 to 21 Mpsi.

7. The extrudable and weldable matrix alloy composite of claim 6, wherein the composite has an elasticity modulus value of between 14 to 18 Mpsi.

8. The extrudable and weldable matrix alloy composite of claim 1, wherein the $B_4C$ content is about 0.1 to 9.5 percent by weight.

9. The extrudable and weldable matrix alloy composite of claim 1, wherein the $B_4C$ content is about 35 to 50 percent by weight.

10. The extrudable and weldable matrix alloy composite of claim 1, wherein the reinforcement agent comprises aluminum oxide or silicon carbide.

11. The extrudable and weldable matrix alloy composite of claim 1, wherein the composite has a density of about 2.40 to 2.80 grams per cubic centimeter.

12. The extrudable and weldable matrix alloy composite of claim 1, wherein the composite has a tensile strength of about 10–110 kpsi.

13. The extrudable and weldable matrix alloy composite of claim 12, wherein the composite has a tensile strength of about 10–90 kpsi.

14. The extrudable and weldable matrix alloy composite of claim 12, wherein the composite has a tensile strength of about 10–70 kpsi.

15. The extrudable and weldable matrix alloy composite of claim 14, wherein the composite has a tensile strength of about 60–110 kpsi.

16. The extrudable and weldable matrix alloy composite of claim 1, wherein the composite has a thermal conductivity of about 60 to 170 W/m° K.

17. The extrudable and weldable matrix alloy composite of claim 1, wherein the composite has a thermal expansion coefficient of about 9 to 21 ppm/° C.

18. An extrudable and weldable matrix alloy composite comprising:
   a) a base material metal of about 50 to 99.9% by weight,
   b) silicon carbide of about 0.1 to 50% by weight, the silicon carbide being substantially homogeneously distributed among the metal, forming close grain boundaries therewith; and
   c) less than about 3.0% by weight of at least one metal having an intermetallic phase temperature lower than the melting point of the base material metal, the metal being included with the boron carbide during its production to provide a chelating opportunity for the base material metal.

19. The extrudable and weldable matrix alloy composite of claim 18, further comprising a reinforcement agent of up to 30% by weight.

20. The extrudable and weldable matrix alloy composite of claim 19, wherein the reinforcement agent is in an amount of betweenn 0.5 and 5%.

21. The extrudable and weldable matrix alloy composite of claim 18, wherein the base material metal is selected from the group comprising aluminum, titanium and alloys thereof.

22. The extrudable and weldable matrix alloy composite of claim 21, wherein the aluminum alloy comprises aluminum alloy 6092 or aluminum alloy 7093.

23. The extrudable and weldable matrix alloy composite of claim 18, wherein the composite has an elasticity modulus value of between 10 to 21 Mpsi.

24. The extrudable and weldable matrix alloy composite of claim 18, wherein the composite has an elasticity modulus value of between 14 to 18 Mpsi.

25. The extrudable and weldable matrix alloy composite of claim 18, wherein the reinforcement agent comprises aluminum oxide.

26. The extrudable and weldable matrix alloy composite of claim 18, wherein the composite has a density of about 2.60 to 3.00 grams per cubic centimeter.

27. The extrudable and weldable matrix alloy composite of claim 18, wherein the composite has a tensile strength of about 10–110 kpsi.

28. The extrudable and weldable matrix alloy composite of claim 18, wherein the composite has a tensile strength of about 10–90 kpsi.

29. The extrudable and weldable matrix alloy composite of claim 18, wherein the composite has a tensile strength of about 10–60 kpsi.

30. The extrudable and weldable matrix alloy composite of claim 18, wherein the composite has a tensile strength of about 60–100 kpsi.

* * * * *